United States Patent [19]

Peters et al.

[11] Patent Number: 4,921,685

[45] Date of Patent: May 1, 1990

[54] METHOD FOR METHANE CONVERSION

[75] Inventors: William A. Peters, Lexington; Jack B. Howard, Winchester, both of Mass.

[73] Assignee: Massachusetts Institute of Technology, Cambridge, Mass.

[21] Appl. No.: 283,401

[22] Filed: Dec. 12, 1988

[51] Int. Cl.$^5$ .............................................. C01B 31/30
[52] U.S. Cl. .................................................... 423/439
[58] Field of Search ........................................ 423/439

[56] References Cited

U.S. PATENT DOCUMENTS 2,729,689  1/1956  Blanchard et al. ................ 423/439

OTHER PUBLICATIONS

Bailar (et al.), Comprehensive Inorganic Chemistry, vol. 1, p. 1207 (1973).

Primary Examiner—Asok Pal
Attorney, Agent, or Firm—George W. Neuner

[57] ABSTRACT

A method for volumetric reduction of gaseous methane to form magnesium carbide is disclosed. A mixture containing methane and magnesium oxide is reacted at a temperature of 1400° C. or greater to form magnesium tricarbide and by-product gases. The carbide can be hydrolyzed to form hydrocarbons that are useful as chemical feedstocks as fuels for combustion, etc. $C_3$ hydrocarbons such as those produced by hydrolysis of magnesium tricarbide can be reacted to form benzene using a dehydrocyclization catalyst.

15 Claims, No Drawings

METHOD FOR METHANE CONVERSION

BACKGROUND OF THE INVENTION

This invention relates to methods for methane conversion to products such as chemical feedstocks, transportable solids and liquids, or other combustible fuels, and particularly to processes for converting methane to magnesium tricarbide, hydrolysis of magnesium tricarbide to $C_3H_4$ hydrocarbon, and condensation/dehydrocyclization of $C_3H_4$ to benzene, or the like.

Methane is the major constituent of natural gas and is a significant domestic fuel and chemical feedstock resource in the United States and other countries. There has been strong interest in developing new processes for converting methane to other useful products of potentially higher value for energy production, chemical manufacture, etc. Furthermore, a significant fraction of the world supply of methane occurs as so-called "remote" gas. "Remote" gas is natural gas found at locations "distant" (1000 to more than 12,000 miles) from major markets. Significant quantities (>10 quads/yr) of remote gas are currently available dry or as a co-product of crude petroleum recovery. High transportation costs exclude remote gas from most major international fuel and chemical markets unless significant volumetric energy densification can be economically achieved. Simple compression to form compressed natural gas (CNG) is economically viable for shipping distances up to about 1000 miles. Longer transport distances demand more severe processing such as direct liquefaction (LNG production) or chemical conversion to other liquids such as methanol or Fischer-Tropsch (FT) hydrocarbons.

Methanol and FT liquids expand remote gas market options to utility and transportation fuels and to chemicals manufacture. However, established technologies generate methanol and FT hydrocarbons indirectly, by catalytically upgrading synthesis gas, expensively manufactured by reforming the remote gas. Thus there is now extensive research and development interest in new technologies for "direct" conversion of remote gas to economically transportable products.

Kim, et al., in *Ind. Eng. Chem. Proesss Des. Dev.*, Vol. 18, No. 2 (1979), discussed the production of calcium carbide by passing a presized suspension of finely divided lime in methane or ethylene, or of finely divided lime and a bituminous coal in hydrogen, through a rotating-arc reactor.

However, there still exists a need for processes to economically upgrade methane into other useful products including products having economically transportable and usable forms.

SUMMARY OF THE INVENTION

The present invention provides a means for converting methane to a readily transportable solid which can be hydrolyzed at its market site to provide a useful hydrocarbon feedstock. In accord with the present invention, a method for carbon densification of methane comprises reacting a feed stream comprising magnesium oxide (MgO) and methane at a temperature of about 1400° C. or greater to form magnesium tricarbide ($Mg_2C_3$) and subsequently, preferably, rapidly quenching the reaction products to a temperature of about 700° C. or less. The resulting $Mg_2C_3$ can be readily transported to a market site and there hydrolyzed to propyne (methyl acetylene, $CH_3C\equiv CH$) or 1,2-propadiene (allene, $H_2C=C=CH_2$), which can be used, e.g., as feedstocks for chemical processes, as fuels for combustion, etc.

The present invention also provides a method for the production of benzene from the hydrolysis products of $Mg_2C_3$. Thus, in accord with another embodiment of the invention, 1,2-propadiene and/or propyne are reacted at a temperature of at least 100° C., preferably in the range of from about 100° C. to about 700° C. in contact with a dehydrocyclization catalyst to dehydrogenate and cyclically isomerize the reactants thereby forming benzene. Bifunctional catalysts such as, for example, platinum (or platinum and rhenium) supported on acidified alumina having the metallic sites for catalyzing dehydrogenation and the acidic sites for catalyzing cyclic isomerization (in this case dimerization), are preferred.

DETAILED DESCRIPTION OF THE INVENTION AND THE PREFERRED EMBODIMENTS

Volumetric densification of initially gaseous methane, in accord with the present invention, is accomplished by reacting magnesium oxide or a magnesium oxide precursor material with methane at temperatures of about 1400° C. or greater, preferably at least about 1500° C., to produce magnesium tricarbide. The magnesium oxide (MgO) can be used as a reaction grade chemical or can be in the form of a MgO containing mineral such as dolomite. Magnesium oxide precursors include materials that decompose or dehydrate to form MgO such as magnesium hydroxide, magnesium carbonate, etc. and the like. Preferably, finely divided MgO or MgO precursor is entrained in a methane gas stream and heated to 1400° C. or above, thereby producing magnesium tricarbide and by-products according to the reaction:

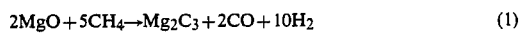

$$2MgO + 5CH_4 \rightarrow Mg_2C_3 + 2CO + 10H_2 \qquad (1)$$

Some magnesium carbide ($MgC_2$) may also be formed according to the reaction:

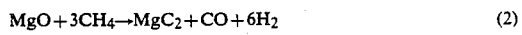

$$MgO + 3CH_4 \rightarrow MgC_2 + CO + 6H_2 \qquad (2)$$

However, carrying out the reaction at temperatures of about 1400° C. or more, in accord with the invention, preferentially produces $Mg_2C_3$. Thus, the preferred methods of the present invention produce more than 50% $Mg_2C_3$, more preferably at least 90% $Mg_2C_3$, and most preferably produce substantially all $Mg_2C_3$ from the Mg in the feed stream.

After the reaction, the products are rapidly quenched to a temperature of about 700° C. or less, preferably at least 500° C. or lower, to prevent decomposition of the $Mg_2C_3$. By rapid quenching, it is meant that the temperature is lowered about 700 to 1300 centigrade degrees in time periods of about one-tenth to one second.

Preferably, the reaction is carried out in a flow reactor where the gas stream is preheated, e.g. by heat exchange with the reaction product stream. The reaction temperature can be achieved in the reaction zone of the reactor by using as a source of energy combustion of methane gas alone or with the separated carbon monoxide and/or hydrogen from the reaction product stream, thereby heating the feed stream. Alternatively, the energy could be used to drive a generator to generate electricity for a discharge arc for the reaction, if desired. The hydrogen by-product can also be used to generate electricity using fuel cells.

The particulate $Mg_2C_3$ is separated from the reactor product stream by conventional separation techniques, e.g., a cyclone separator. A stoichiometric excess of methane in the feed stream to the reactor helps to ensure complete reaction of MgO to $Mg_2C_3$, whereas an excess of MgO helps complete reaction of the methane to form magnesium carbide. The MgO can be pretreated with carbon powder or coal dust before entraining it in the methane reactant stream.

$Mg_2C_3$ is conveniently converted into hydrocarbons by hydrolysis in accord with the following reactions:

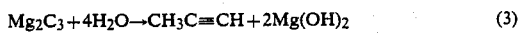

$$Mg_2C_3 + 4H_2O \rightarrow CH_3C\equiv CH + 2Mg(OH)_2 \qquad (3)$$

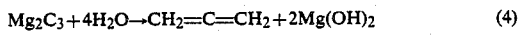

$$Mg_2C_3 + 4H_2O \rightarrow CH_2=C=CH_2 + 2Mg(OH)_2 \qquad (4)$$

The resulting $Mg(OH)_2$ can be calcined to regenerate MgO or can be recycled directly into the methane feed stream to produce carbide.

1,2-Propadiene isomerizes to methylacetylene in the presence of strong bases such as sodamide in liquid ammonia, or KOH in ethanol. Thus, conversion of methane to magnesium tricarbide provides a means of converting remote gas to a $C_3$ hydrocarbon. Both $C_3$ hydrocarbon hydrolysis products are gases at room temperature and have high volumetric heating values. Thus, they are useful as fuels. They are also useful as chemical feedstocks, e.g., they are monomeric building blocks for use in reactions to form higher hydrocarbons including linear hydrocarbons and cyclic hydrocarbons such as, for example, benzene, and the like.

Further, in accord with another embodiment of the present invention, 1,2-propadiene and/or methylacetylene are reacted to form benzene in accord with the following reaction:

$$2C_3H_4 \rightarrow C_6H_6 + H_2 \qquad (5)$$

Thus, the $C_3$ hydrolysis products of $Mg_2C_3$ are reacted over dehydrocyclization catalyst at temperatures of about 100° C. or greater, preferably at a temperature in the range of from about 100° C. to about 700° C., more preferably in the range of from about 300° C. to about 600° C., and most preferably in the range of from about 450° C. to about 550° C.

Any catalyst or mixture of catalysts that achieve dimerization, dehydrogenation, and cyclization to form benzene can be used. Suitable catalysts are described, for example, by C. N. Satterfield at pages 247-250 of *Heterogeneous Catalysis in Practice*, McGraw-Hill, New York (1980) and by B. C. Gates, J. R. Katzer, and G. C. A. Schuit at pages 283-287 of *Chemistry of Catalytic Process*, McGraw-Hill, New York (1979). Preferred catalysts for the formation of benzene in accord with reaction (5) above are bifunctional catalysts such as, e.g., platinum (or platinum and rhenium) supported on acidified alumina, and the like. Such catalysts have metallic sites for catalyzing dehydrogenation and acid sites for catalyzing the isomerization. The benzene can readily be separated from the hydrogen by-product by cooling. Conveniently, the hydrogen by-product can be used to generate energy for the reaction or for a variety of other uses. For instance, it can be used to power fuel cells to produce electricity which can be sold or used to supply energy for the processes of the present invention.

The following examples are provided to further illustrate the present invention.

Example I. Production of Magnesium Tricarbide ($Mg_2C_3$ From Methane and Magnesium Oxide A mixture of methane ($CH_4$) gas and entrained magnesium oxide (MgO) particles, in the molar ratio 5:3 (i.e. five moles of $CH_4$ per three moles of MgO) is fed continuously to a tubular reaction chamber, maintained at a temperature of about 1800° C. Before feeding, the MgO particles are presized in the approximate range 38-45 um using standard sieves (i.e. 325, +400 mesh). The reaction chamber is about 1 inch ID and fabricated from a suitable high temperature refractory material able to withstand high temperature reducing environments. The total inlet pressure of methane is about 1.3 atm. (absolute). The length of the reaction chamber and the methane flow rate are chosen so that the residence time of the reactants (i.e. the $CH_4$ and MgO) at, or near 1800° C., is about 1 second.

Immediately upon exiting the reaction chamber the products, and unconverted reactants, are "rapidly" (i.e. in about 0.1 to 1 second) cooled to 600° C. by innundating the reactor effluent stream with a large excess of initially cold (i.e. initially at or near room temperature) quench gas—for example additional methane, in the ratio six moles of room temperature methane per mole of methane fed to the conversion reactor. The cooled (approximately 600 C) reactor effluent stream is then conveyed through a cyclone for separation of the solid particulates (including product $Mg_2C_3$ and unconverted MgO) from the reactant, quench, and product gases ($CH_4$, CO, $H_2$, etc.). The particulates are collected in a vessel connected by a tube to the bottom outlet of the cyclone, the cyclone effluent gases are further cooled if necessary, and then conveyed to suitable gas separation and recovery equipment (for example cryogenic separators, membranes, sorption-desorption beds) for recovery of $H_2$ and CO, and recycle of the $CH_4$ for use as reactor feed.

Throughout the process, meticulous care should be exercised to prevent contact of the $Mg_2C_3$, or other carbide by-products, with water or steam. This is to prevent hydrolysis of these compounds to potentially explosive hydrocarbon gases, such as, in the case of $Mg_2C_3$, methylacetylene.

Example II. Production of Benzene by Condensation/Dehydrocyclization of Methylacetylene A one inch internal diameter, 15 inch long, stainless steel tubular reactor, thoroughly cleaned and certified for use with acetylene and related compounds is employed. Because of potential for formation of explosive acetylide compounds, no parts of copper, silver, brass, or bronze are used. The reactor is packed over 12 inches of its length with pellets of a catalyst containing platinum metal on acidified alumina having a size consistency as used in the petroleum industry for catalytic reforming of paraffins to aromatics. To reduce the potential for explosion of methylacetylene or other gaseous acetylenic compounds, regions of dead volume in the reactor system, including for example the remaining unpacked regions of the reactor itself, are packed with quartz or stainless steel beads. Using a tubular furnace, the reactor is preheated to 500 C and then maintained within 10 C of that temperature during operation. Methylacetylene ($C_3H_4$) is introduced to the reactor at an inlet partial pressure of 0.8 atm (abs.). A suitable carrier gas, such as molecular nitrogen ($N_2$) is employed to provide sufficient total inlet pressure (up to about 1.5 atm) to propel the reactants and products through the reactor and downstream products recovery equipment. The total gas flowrate ($CH_4$ and $N_2$) is adjusted so that the nominal $C_3H_4$ contact time (space time) with the catalyst is between 2 and 10 seconds.

The effluent of the reactor is immediately directed through a conventional cooled condenser made from a vertical stainless steel tube surrounded by a cooling jacket continuously flushed with cold water allowing condensation to product benzene as a liquid, and subsequent accumulation of that liquid benzene in a collection sump connected to the bottom of the condenser. In the condenser, liquid benzene product is separated from the effluent gases—by-product $H_2$, $N_2$ carrier, and unconverted methylacetylene. If desired, the hydrogen may be further separated and recovered from these other two gases by cryogenic or sorption-desorption processes. The remaining methylacetylene, and $N_2$ carrier, can be recycled to the catalytic reactor for further conversion of the methylacetylene to benzene. The liquid benzene product is recovered from the collection vessel connected to the condenser.

The invention has been described in detail including the preferred embodiments thereof. However, it is appreciated that those skilled in the art, upon consideration of this specification, may make modifications and improvements within the spirit and scope of the appended claims.

We claim:

1. A method for carbon densification of methane, said method comprising reacting a mixture comprising methane and a magnesium oxide at a reaction temperature of about 1400° C. or more to form magnesium tricarbide and by-product gas comprising hydrogen.

2. The method of claim 1, further comprising the step of hydrolyzing the resulting magnesium tricarbide.

3. The method of claim 1, further comprising the step of heating a mixture of particulate magnesium oxide entrained in a methane gas stream.

4. The method of claim 3 wherein energy for the heating step is provided, at least in part, by combustion of methane.

5. The method of claim 3 wherein energy for the heating step is provided, at least in part, by an electrical discharge.

6. The method of claim 5 wherein the electricity for the electrical discharge is provided, at least in part, by conversion of the hydrogen by-product gas in a fuel cell.

7. The method of claim 5 wherein the electricity for the electrical discharge is provided, at least in part, by combustion of methane to drive a generator.

8. The method of claim 3 wherein energy for the heating step is provided, at least in part, by combustion of by-product gas.

9. The method of claim 1 wherein the reaction temperature is at least 1500° C.

10. The method of claim 1, further comprising the step of rapidly quenching the magnesium tricarbide and by-product gas to a temperature of about 700° C. or less.

11. The method of claim 1, further comprising the step of rapidly quenching the magnesium tricarbide and by-product gas to a temperature of at least about 500° C. or lower.

12. A method for carbon densification of methane, said method comprising the steps of (A) preheating a mixture comprising MgO entrained in methane; (B) reacting the MgO and methane at a reaction temperature of about 1400° C. or more to form reaction products comprising $Mg_2C_3$; and (C) rapidly quenching the reaction products to a temperature of about 700° C. or less.

13. The method of claim 12 wherein the energy for the preheating step is supplied, at least in part, by heat exchange with the reaction products 14. The method of claim 12, further comprising the step of hydrolyzing the $Mg_2C_3$, thereby forming $C_3$ hydrocarbons and $Mg(OH)_2$.

15. The method of claim 14, further comprising the steps of calcining the $Mg(OH)_2$ to regenerate MgO and recycling the MgO.

* * * * *